(12) United States Patent
Kramer

(10) Patent No.: US 11,571,124 B2
(45) Date of Patent: Feb. 7, 2023

(54) RETINAL IMAGING SYSTEM WITH USER-CONTROLLED FIXATION TARGET FOR RETINAL ALIGNMENT

(71) Applicant: Verily Life Sciences LLC, South San Francisco, CA (US)

(72) Inventor: Ryan Kramer, San Francisco, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 385 days.

(21) Appl. No.: 16/821,936

(22) Filed: Mar. 17, 2020

(65) Prior Publication Data

US 2020/0305711 A1   Oct. 1, 2020

Related U.S. Application Data

(60) Provisional application No. 62/824,210, filed on Mar. 26, 2019.

(51) Int. Cl.
  *A61B 3/15* (2006.01)
  *A61B 3/00* (2006.01)
  *G06T 7/00* (2017.01)

(52) U.S. Cl.
  CPC ............ *A61B 3/152* (2013.01); *A61B 3/0058* (2013.01); *A61B 3/0075* (2013.01); *A61B 3/0083* (2013.01); *A61B 3/0091* (2013.01); *G06T 7/0012* (2013.01); *G06T 2207/30041* (2013.01)

(58) Field of Classification Search
  CPC ..... A61B 3/152; A61B 3/0058; A61B 3/0075; A61B 3/0083; A61B 3/0091; A61B 3/12; G06T 7/0012; G06T 2207/30041

USPC .......................................................... 351/208
  See application file for complete search history.

(56) References Cited

U.S. PATENT DOCUMENTS

| 5,585,873 A | 12/1996 | Shalon et al. |
| 7,524,062 B2 | 4/2009 | Iwa et al. |
| 7,677,730 B2 | 3/2010 | Shimizu |
| 8,421,855 B2 | 4/2013 | Buckland et al. |
| 8,637,882 B2 | 1/2014 | Stoyan |

(Continued)

FOREIGN PATENT DOCUMENTS

WO      2018/119077 A1     6/2018

OTHER PUBLICATIONS

International Search Report and Written Opinion, dated Jun. 9, 2020, for corresponding International Patent Application No. PCT/US2020/024193, 9 pages.

(Continued)

*Primary Examiner* — Mohammed A Hasan
(74) *Attorney, Agent, or Firm* — Christensen O'Connor Johnson Kindness PLLC

(57) ABSTRACT

Retinal imaging systems and methods are described. In an embodiment, the retinal imaging system includes an eyepiece lens assembly; an image sensor adapted to acquire a retinal image of an eye through the eyepiece lens assembly; a dynamic fixation target optically coupled to the eyepiece lens assembly such that the dynamic fixation target is viewable through the eyepiece lens assembly; and a controller communicatively coupled to the image sensor and the dynamic fixation target. In an embodiment, the dynamic fixation target includes a display where an image generated by the display is controlled by a position of a user's eye relative to the eyepiece lens assembly.

20 Claims, 11 Drawing Sheets

(56) References Cited

U.S. PATENT DOCUMENTS

| | | | |
|---|---|---|---|
| 8,708,490 B2 | 4/2014 | Baranton et al. | |
| 9,039,176 B2 | 5/2015 | Honda et al. | |
| 9,254,084 B2 | 2/2016 | Yoshino | |
| 9,370,303 B2 | 6/2016 | Tanaka et al. | |
| 9,498,126 B2 | 11/2016 | Wang | |
| 9,743,832 B2 | 8/2017 | de Paz Sicam et al. | |
| 9,918,629 B2 | 3/2018 | Wang | |
| 11,389,060 B2 | 7/2022 | Glik et al. | |
| 2012/0069302 A1* | 3/2012 | Juhasz | A61B 3/117 351/221 |
| 2013/0181976 A1 | 7/2013 | Dastmalchi et al. | |
| 2017/0100032 A1* | 4/2017 | Zakariaie | A61B 3/145 |
| 2017/0164830 A1 | 6/2017 | Huang et al. | |
| 2017/0169658 A1 | 6/2017 | Froy et al. | |
| 2018/0008460 A1 | 1/2018 | Tanzer | |
| 2019/0046031 A1 | 2/2019 | Kramer et al. | |
| 2019/0110677 A1 | 4/2019 | Walsh et al. | |
| 2019/0125184 A1 | 5/2019 | Kramer et al. | |
| 2019/0199893 A1 | 7/2019 | Kramer et al. | |

OTHER PUBLICATIONS

"Welch Allyn RetinaVue 100 Imager, Directions for use, Software version 6.XX," Welch Allyn, Material No. 411492. (116 pages).

"DualAlign i2k Retina, Registering and Aligning Fundus Images," TOPCON. (2 pages).

Muqit et al., "Optos-guided pattern scan laser (Pascal)-targeted retinal photocoagulation in proliferative diabetic retinopathy," Acta Ophthalmologica, 31:251-258, 2013.

Klein et al., "Megahertz OCT for ultrawide-field retinal imaging with a 1050nm Fourier domain mode-locked laser," Optics Express, 19(4)3044-3062, Feb. 14, 2011.

Dehoog et al., "Optimal parameters for retinal illumination and imaging in fundus cameras," Applies Optics, 47 (36):6769-6777, Dec. 20, 2008.

"Instruction Manual, Retinal Camera, TRC-50X," Topcon. (46 pages).

"Topcon Introduces the TRC-NW400 Non-mydriatic Retinal Camera with Fully Automatic Functions for Alignmnet, Focusing and Capturing Color Retinal Images," OphthalmologyWeb, retrieved from ,https://www.ophthalmologyweb.com/1315-News/167901-Topcon-Introduces-the-TRC-NW400-Non-mydriatic-Retinal-Camera-with-Fully-Automatic-Functions-for-Alignment-Focusing-and-Capturing-Color-Retinal-Images/> on Sep. 10, 2018. (2 pages).

"Instruction Manual, Retinal Camera, TRC-50DX," Topcon. (80 pages).

"TRC-NW7SF Mark II, Mydriatic/Non-Mydriatic Retinal Camera," Topcon. (4 pages).

U.S. Appl. No. 17/839,951, filed Jun. 14, 2022, 37 pages.

* cited by examiner

RETINAL IMAGING SYSTEM WITH USER-CONTROLLED FIXATION TARGET FOR RETINAL ALIGNMENT

CROSS-REFERENCE TO RELATED APPLICATION

This application claims the benefit of U.S. Provisional Application No. 62/824,210, filed Mar. 26, 2019, which is hereby incorporated by reference in its entirety.

TECHNICAL FIELD

This disclosure relates generally to retinal imaging technologies and, in particular, but not exclusively, relates to fixation targets for retinal imaging.

BACKGROUND INFORMATION

Retinal imaging is a part of basic eye exams for screening, field diagnosis, and progress monitoring of many retinal diseases. A high-fidelity retinal image is important for accurate screening, diagnosis, and monitoring. Bright illumination of the posterior interior surface of the eye (i.e., retina) through the pupil improves image fidelity but often creates optical aberrations or image artifacts, such as corneal reflections, iris reflections, or lens flare, if the retinal camera and illumination source are not adequately aligned with the eye. Simply increasing the brightness of the illumination does not overcome these problems, but rather makes the optical artifacts more pronounced, which undermines the goal of improving image fidelity.

Accordingly, camera alignment is very important, particularly with conventional retinal cameras, which typically have a very limited eyebox due to the need to block the deleterious image artifacts listed above. The eyebox for a retinal camera is a three-dimensional region in space typically defined relative to an eyepiece of the retinal camera and within which the center of a pupil or cornea of the eye should reside to acquire an acceptable image of the retina. The small size of conventional eyeboxes makes retinal camera alignment difficult and patient interactions during the alignment process often strained.

Various solutions have been proposed to alleviate the alignment problem. For example, moving/motorized stages that automatically adjust the retina-camera alignment have been proposed. However, these stages tend to be mechanically complex and substantially increase the cost of a retinal imaging platform. An effective and low-cost solution for efficiently and easily achieving eyebox alignment of a retinal camera would improve the operation of retinal cameras.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system; non-transitory, machine-readable storage medium; and method of dynamically adjusting a fixation target to encourage alignment of an eye relative to an eyepiece lens assembly are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
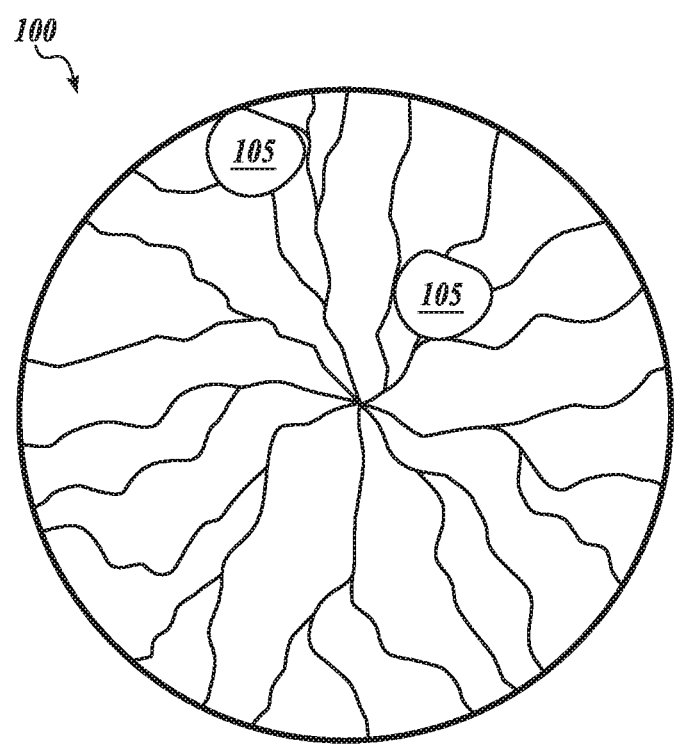
FIG. 1 illustrates a retinal image including a demonstrative image artifact due to misalignment of a retinal camera.

High-fidelity retinal images are important for screening, diagnosing, and monitoring many retinal diseases. To this end, reducing or eliminating instances of image artifacts that occlude or otherwise malign portions of the retinal image is desirable. FIG. 1 illustrates an example retinal image 100 with multiple image artifacts 105. These image artifacts 105 may arise when misalignment between the retinal imaging system and the eye permit stray light and deleterious reflections from the illumination source to enter the imaging path and ultimately are captured by the image sensor with the retinal image light. Misalignment can lead to deleterious corneal/iris reflections, refractive scattering from the crystalline lens, occlusion of the imaging aperture, optical aberrations due to off axis passage through the crystalline lens, the blockage of imaging light by the iris, and/or other issues. Conventional imaging systems have relatively small eyeboxes, which require precise alignment to avoid image artifacts from entering the image path.

Embodiments described herein utilize a dynamic fixation target not just as a static point to stabilize a patient's fixation, select the center ray of the patient's field of view (FOV), and lock the patient accommodation at a fixed depth, but also to aid in the alignment and retinal image optimization. In particular, embodiments described herein incorporate a dynamic fixation target that adjusts in real-time based upon a position of an eye of a user relative to an eyepiece lens assembly of the retinal imaging system. The dynamic adjustment of the fixation target encourages repositioning of the eye position relative to the eyepiece lens assembly to compensate for misalignment between the eyepiece lens assembly and the patient's eye. Accordingly, in an aspect, the present disclosure provides a retinal imaging system for aligning an eye within an eyebox. In an embodiment, the retinal imaging systems of the present disclosure include an eyepiece lens assembly; an image sensor adapted to acquire a retinal image of an eye through the eyepiece lens assembly; a dynamic fixation target optically coupled to the eyepiece lens assembly such that the dynamic fixation target is viewable through the eyepiece lens assembly; and a controller communicatively coupled to the image sensor and the dynamic fixation target. In an embodiment, the controller includes logic that, when executed by the controller, causes the retinal imaging system to perform operations including: acquiring a first image of the eye; analyzing the first image to determine whether any misalignment between the eye and the eyepiece lens assembly is greater than a threshold misalignment; in response to determining whether any misalignment is greater than the threshold misalignment, adjusting the dynamic fixation target based on a position of the eye relative to the eyepiece lens assembly; and acquiring the retinal image of the eye while the eye is positioned within the threshold misalignment.

As discussed further herein, such dynamic adjustment of the fixation target can include presenting strategic goals to a user, such as in the form of a video game or other visual representation, to encourage alignment of the eye and the eyepiece lens assembly.

Figure 2:
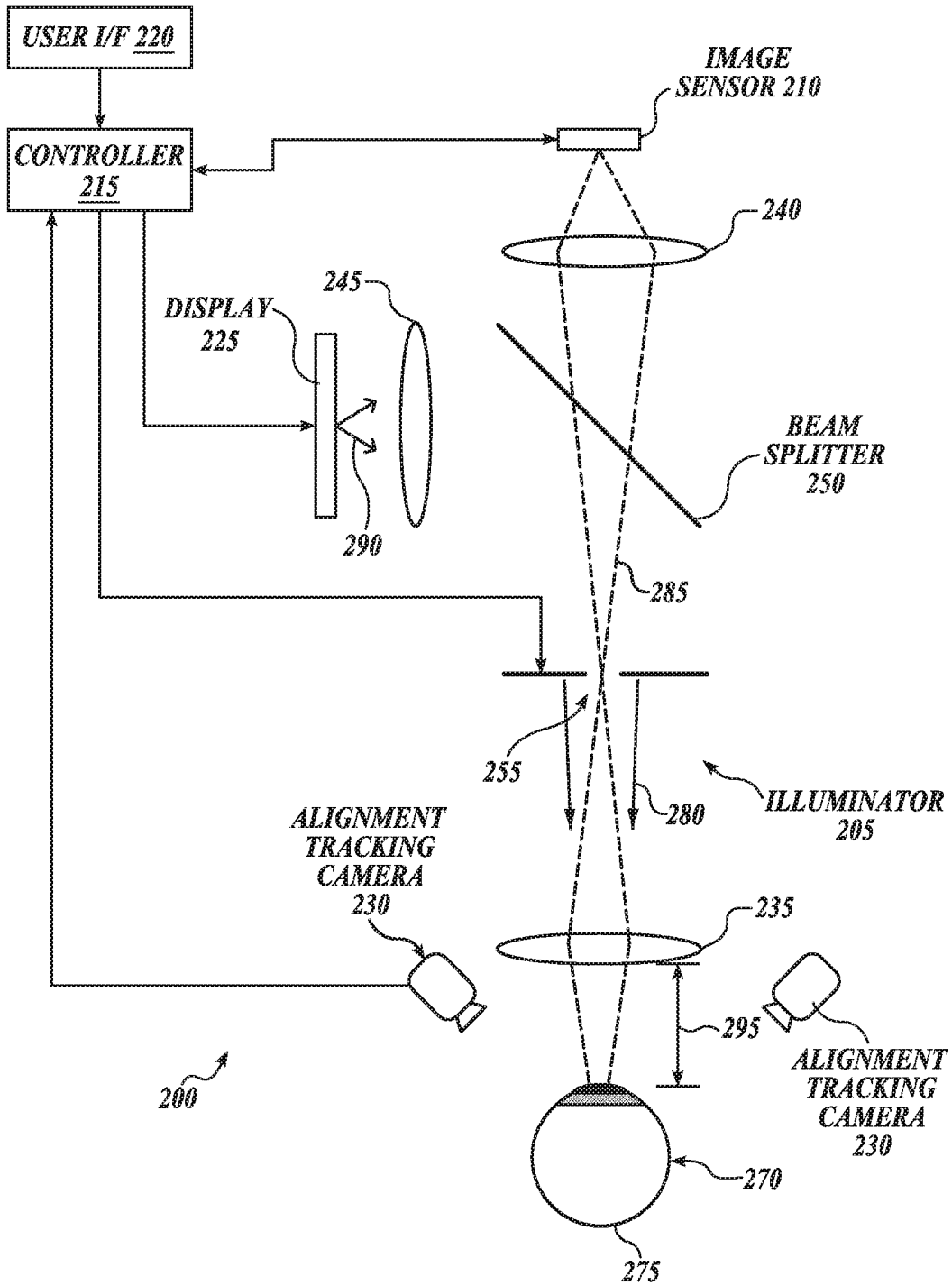
FIG. 2 illustrates a retinal imaging system with a dynamic fixation target, in accordance with an embodiment of the disclosure.

FIG. 2 illustrates a retinal imaging system 200 with a dynamic fixation target, in accordance with an embodiment of the disclosure. The illustrated embodiment of retinal imaging system 200 includes an illuminator 205, an image sensor 210 (also referred to as a retinal image sensor), a controller 215, a user interface 220, a display 225, an alignment tracking camera(s) 230, and an optical relay system. The illustrated embodiment of the optical relay system includes lens assemblies 235, 240, and 245 and a beam splitter 250. The illustrated embodiment of illuminator 205 comprises a ring illuminator defining a center aperture 255.

The optical relay system serves to direct (e.g., pass or reflect) illumination light 280 output from illuminator 205 along an illumination path through the pupil of eye 270 to illuminate retina 275 while also directing image light 285 of retina 275 (i.e., the retinal image) along an imaging path to image sensor 210. Image light 285 is formed by the scattered reflection of illumination light 280 off of retina 275. In the illustrated embodiment, the optical relay system further includes beam splitter 250, which passes at least a portion of image light 285 to image sensor 210 while also optically coupling dynamic fixation target including display 225 to eyepiece lens assembly 235 and directing display light 290 output from display 225 to eye 270. Beam splitter 250 may be implemented as a polarized beam splitter, a non-polarized beam splitter (e.g., 90% transmissive and 10% reflective, 50/50 beam splitter, etc.), a dichroic beam splitter, or otherwise. The optical relay system includes a number of lenses, such as lenses 235, 240, and 245, to focus the various light paths as needed. For example, lens 235 may include one or more lensing elements that collectively form an eyepiece lens assembly 235 that is displaced from the cornea of eye 270 by an eye relief 295 during operation. Lens 240 may include one or more lens elements for bringing image light 285 to a focus on image sensor 210. Lens 245 may include one or more lens elements for focusing display light 290. It should be appreciated that the optical relay system may be implemented with a number and variety of optical elements (e.g., lenses, reflective surfaces, diffractive surfaces, etc.) and may vary from the configuration illustrated in FIG. 2.

The dynamic fixation target may be an image, a moveable physical object, and combinations thereof. In one embodiment, the dynamic fixation target includes the display 225, such as including display light 290 output from display 225. The dynamic fixation target not only can aid with obtaining alignment between retinal imaging system 200 and eye 270 by providing visual feedback to the patient but may also give the patient a fixation target upon which the patient can accommodate and stabilize their vision. The dynamic fixation target may be moved by translating the image of the fixation target about display 225 as desired (e.g., moving the fixation target up/down or left/right on display 225).

Display 225 may be implemented with a variety of technologies including a liquid-crystal display (LCD), light-emitting diodes (LEDs), various illuminated shapes (e.g., an illuminated cross or concentric circles), or otherwise. Of course, the dynamic fixation target may be implemented in other manners than a virtual image on a display. For example, the dynamic fixation target may be a physical object (e.g., crosshairs, etc.) that is physically manipulated.

Controller 215 is coupled to image sensor 210, display 225, illuminator 205, and alignment tracking camera 230 to choreograph their operation. Controller 215 may include software/firmware logic executing on a microcontroller, hardware logic (e.g., application specific integrated circuit, field programmable gate array, etc.), or a combination of software and hardware logic. Although FIG. 2 illustrates controller 215 as a distinct functional element, the logical functions performed by controller 215 may be decentralized across a number hardware elements. Controller 215 may further include input/output (I/O ports), communication systems, or otherwise. Controller 215 is coupled to user interface 220 to receive user input and provide user control over retinal imaging system 200. User interface 220 may include one or more buttons, dials, feedback displays, indicator lights, etc.

Image sensor 210 may be implemented using a variety of imaging technologies, such as complementary metal-oxide-semiconductor (CMOS) image sensors, charged-coupled device (CCD) image sensors, or otherwise. In one embodiment, image sensor 210 includes an onboard memory buffer or attached memory to store/buffer retinal images.

Alignment tracking camera 230 is an optional element that operates to track alignment (or misalignment) between retinal imaging system 200 and eye 270, and in particular, between eyepiece lens assembly 235 and eye 270. Alignment tracking camera 230 may operate using a variety of different techniques to track the relative position of eye 270 to retinal imaging system 200 including pupil tracking, retina tracking, iris tracking, or otherwise. In the illustrated embodiment, alignment tracking camera 230 includes two cameras disposed on either side of eyepiece lens assembly 235 to enable triangulation and obtain X, Y, and Z position information about the pupil or iris. In one embodiment, alignment tracking camera 230 includes one or more infrared (IR) emitters to track eye 270 via IR light while retinal images are acquired with visible spectrum light. In such an embodiment, IR filters may be positioned within the image path to filter the IR tracking light. In some embodiments, the tracking illumination is temporally offset from image acquisition.

Alignment may be measured via retinal images acquired by image sensor 210, or separately/additionally, by alignment tracking camera 230. In the illustrated embodiment, alignment tracking camera 230 is positioned externally to view eye 270 from outside of eyepiece lens assembly 235. In other embodiments, alignment tracking camera 230 may be optically coupled via the optical relay components to view and track eye 270 through eyepiece lens assembly 235.

During operation, controller 215 operates illuminator 205 and retinal image sensor 210 to capture one or more retinal images. Illumination light 280 is directed through the pupil of eye 270 to illuminate retina 275. The scattered reflections from retina 275 are directed back along the image path through aperture 255 to image sensor 210. When eye 270 is properly aligned within the eyebox of retinal imaging system 200, aperture 255 operates to block deleterious reflections and light scattering that would otherwise malign the retinal image while passing the image light itself.

Prior to capturing the retinal image, controller 215 operates display 225 to output a dynamic fixation target to guide a position of the eye 270 relative to the eyepiece lens assembly 235 and to direct the patient's gaze. One or more initial eye images (a.k.a., initial alignment images), either from image sensor 210 or alignment tracking camera 230, are acquired and analyzed to determine the alignment between eye 270 and eyepiece lens assembly 235. These initial alignment images may be illuminated with IR light output from illuminator 205 (or an independent illuminator associated with alignment tracking camera 230) so as not to trigger an iris constriction response, which constricts the imaging path to retina 275. In other embodiments, conventional white light or other chromatic light is used to acquire the initial alignment images. The initial alignment image is then analyzed by controller 215 to identify any misalignment, adjust the dynamic fixation target to encourage alignment of the eye 270, and then acquire one or more subsequent eye images (e.g., retinal images) with image sensor 210. The subsequent images may be full color images, specific chromatic images, or even IR images as desired.

In this regard, in an embodiment, the controller 215 includes logic that when executed by the controller 215 causes the retinal imaging system 200 to perform operations including acquiring a first image of the eye 270; analyzing the first image to determine whether any misalignment between the eye 270 and the eyepiece lens assembly 235 is greater than a threshold misalignment; in response to determining whether the misalignment is greater than the threshold misalignment, adjusting the display 225 based on a position of the eye 270 relative to the eyepiece lens assembly 235; and acquiring the retinal image of the eye 270 while the eye 270 is positioned within the threshold misalignment.

Adjusting the display 225 can be based on a position of the eye 270 relative to the eyepiece lens assembly 235. As discussed further herein, repositioning the eye 270 relative to the eyepiece lens assembly 235 can align the eye 270 with respect to the retinal imaging system 200, particularly the image sensor 210. In this regard, adjusting the display 225 encourages a repositioning of the eye 270 to achieve alignment between the eye 270 and components of the retinal imaging system 200, such as the eyepiece lens assembly 235 and the image sensor 210.

In an embodiment, adjusting the display 225 includes displaying an alignment image with the display 225 based upon a position of the eye 270 relative to the eyepiece lens assembly 235. In an embodiment, displaying the alignment image with the display 225, includes moving an element, such as a virtual element, with the alignment image output by the display 225 based upon a position of the eye 270 relative to the eyepiece lens assembly 235. In this regard, in an embodiment, a position of the eye 270 relative to the eyepiece lens assembly 235 controls the alignment image generated by the display 225 to provide a user with an indication of the position of the eye 270 relative to the eyepiece lens assembly 235.

In an embodiment, an alignment image generated by the display 225 is configured to present one or more strategic goals for a user to achieve alignment of the eye 270 relative to the eyepiece lens assembly 235. In this regard, the alignment image may include a representation of the position of the eye 270 position relative to the eyepiece lens assembly 235 and a representation of an aligned eye position that is under a threshold misalignment. As discussed further herein, such representations of the position of the eye 270 relative to the eyepiece lens assembly 235 and the aligned eye may encourage a user to move their eye 270 relative to the eyepiece lens assembly 235 laterally and/or forward/backward to achieve alignment of the eye 270 with respect to the retinal imaging system 200, particularly the image sensor 210 and eyepiece lens assembly 235. Such lateral and fore/aft alignment of the eye 270 with respect to the image sensor 210 and the eyepiece lens assembly 235 are distinct from a gaze vector of the eye 270 suitable for retinal imaging. In an embodiment, alignment of the eye 270 with respect to the components of the retinal imaging system 200 includes a position of the eye 270 with respect to such components, as well as a gaze vector of the eye 270 and pupil dilation, suitable for retinal imaging.

In an embodiment, one or more portions of the dynamic fixation target moves during alignment of the user's eye 270. A user's eye 270 may tire when focused on a stationary object for a prolonged time. Accordingly, in an embodiment, the display 225 or an alignment image output by the display 225 moves to allow the eye 270 to move as alignment occurs.

As above, the displays of retinal imaging systems of the present disclosure, such as display 225 of retinal imaging system 200, are configured to generate alignment images based upon a position of an eye of a user relative to the eyepiece lens assembly. In that regard, attention is directed to FIGS. 3-10 and 12 in which alignment images, in accordance with an embodiment of the disclosure, are illustrated. In an embodiment, the alignment images are images displayed by a dynamic fixation target based on a position of an eye relative to an eyepiece lens assembly. In an embodiment, the alignment images of FIGS. 3-10 and 12 are examples of alignment images output by display 225 of retinal imaging system 200.

Figure 3:
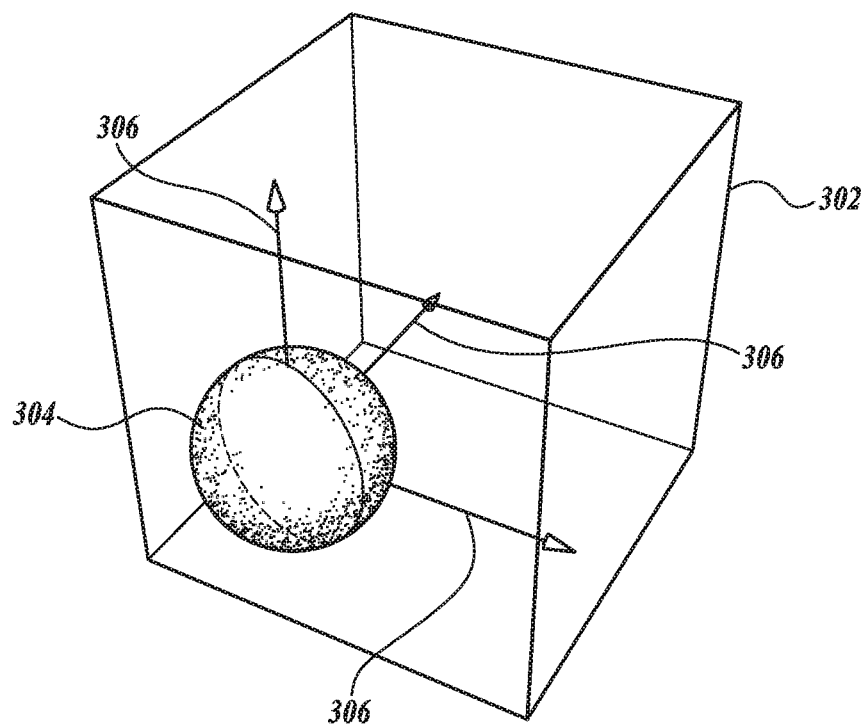
FIG. 3 is an alignment image displayed by a dynamic fixation target based on a position of an eye relative to an eyepiece lens assembly, in accordance with an embodiment of the disclosure.

FIG. 3 is an image displayed by a dynamic fixation target based on a position of an eye relative to an eyepiece lens assembly, in accordance with an embodiment of the disclosure. As shown, the alignment image includes a cube 302, a sphere 304 partially disposed within the cube 302, and a number of arrows 306 emanating from the sphere 304. In an embodiment, a position of the sphere 304 is based on a position of a user's eye, such as a position of the eye relative to an eyepiece lens assembly of a retinal imaging system. In this regard, the alignment image includes a representation of the position of the eye relative to the eyepiece lens assembly and a representation of an aligned eye position that is under the threshold misalignment.

In an embodiment, the cube 302, such as a size and position of the cube 302, is based on a threshold misalignment within which an image suitable for retinal imaging may be obtained. In this regard, the alignment image includes a representation of the threshold misalignment.

In an embodiment, the arrows 306, such as a size and/or direction of the arrows 305, indicate one or more directions/distances along which the user's eye should proceed to bring the eye within the cube 302. Accordingly, in an embodiment, the alignment image includes a representation of a direction in which to move the eye to achieve alignment of the eye with the eyepiece lens assembly.

As the user moves their eye relative to the eyepiece lens assembly, the alignment image displayed by the dynamic fixation target changes based upon such movement, such as to generate an image in which the sphere 304 is within the cube 302, such as when the eye is within the eyebox of the retinal imaging system. In an embodiment, a size of the cube 302 shrinks as the eye moves closer to alignment with respect to the eyepiece lens assembly.

In an embodiment, the size of the cube 302 shrinks in proportion to an alignment between the eye and the eyepiece lens assembly. In this way, a size of the representation of the threshold misalignment changes based on an alignment between the eye and the eyepiece lens assembly. Likewise, in an embodiment, adjusting the dynamic fixation target includes moving an element of the alignment image based upon the position of the eye relative to the eyepiece lens assembly. In this regard, the dynamic fixation target generally encourages alignment of the eye with respect to the eyepiece lens assembly, such as to within a threshold misalignment of the retinal imaging system.

Figure 4:
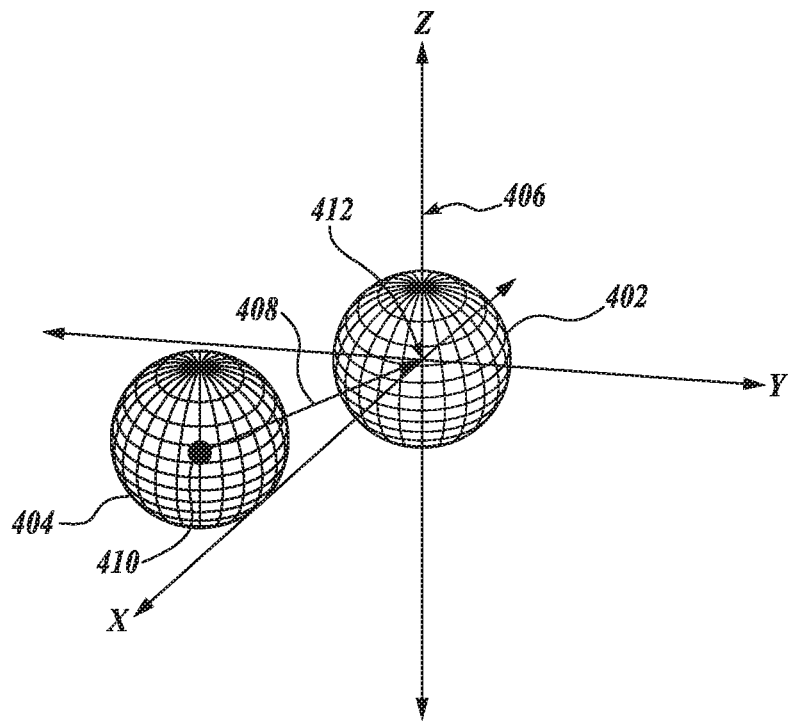
FIG. 4 is an alignment image displayed by a dynamic fixation target based on a position of an eye relative to an eyepiece lens assembly, in accordance with an embodiment of the disclosure.

FIG. 4 is an alignment image displayed by a dynamic fixation target based on a position of an eye relative to an eyepiece lens assembly, in accordance with an embodiment of the disclosure. As shown, the alignment image includes a first sphere 402 at a center 412 of Cartesian coordinates 406, a second sphere 404 disposed away from the center 412 of the Cartesian coordinates 406, and an arrow 408 pointing from a center 410 of the second sphere 404 to the center 412 of the Cartesian coordinates 406. In an embodiment, a position of the second sphere 404 is based on a position of a user's eye, such as a position of the eye relative to an eyepiece lens assembly of a retinal imaging system. In embodiment, a position of the first sphere 402 in the alignment image is based on an ideal alignment of a user's eye relative to the eyepiece lens assembly.

As shown, the second sphere 404 does not entirely overlap with the first sphere 402, indicating a misalignment between the eye and the eyepiece lens assembly. In an embodiment, the arrow 408 indicates one or more directions along which the user's eye should move to achieve alignment of the eye with respect to the eyepiece lens assembly. In this regard, the alignment image presents strategic goals to a user to achieve alignment of the eye with respect to components of the retinal imaging system, such as the eyepiece lens assembly.

In an embodiment, a size of the first sphere 402 changes, such as by shrinking, as the eye achieves alignment with the eyepiece lens assembly. In an embodiment, a size of the second sphere 404 matches the size of the first sphere 402 as alignment between the eye and the eyepiece lens assembly is achieved and the first sphere 402 and second sphere 404 are shown to overlap entirely or to overlap to a greater extent.

Figure 5:
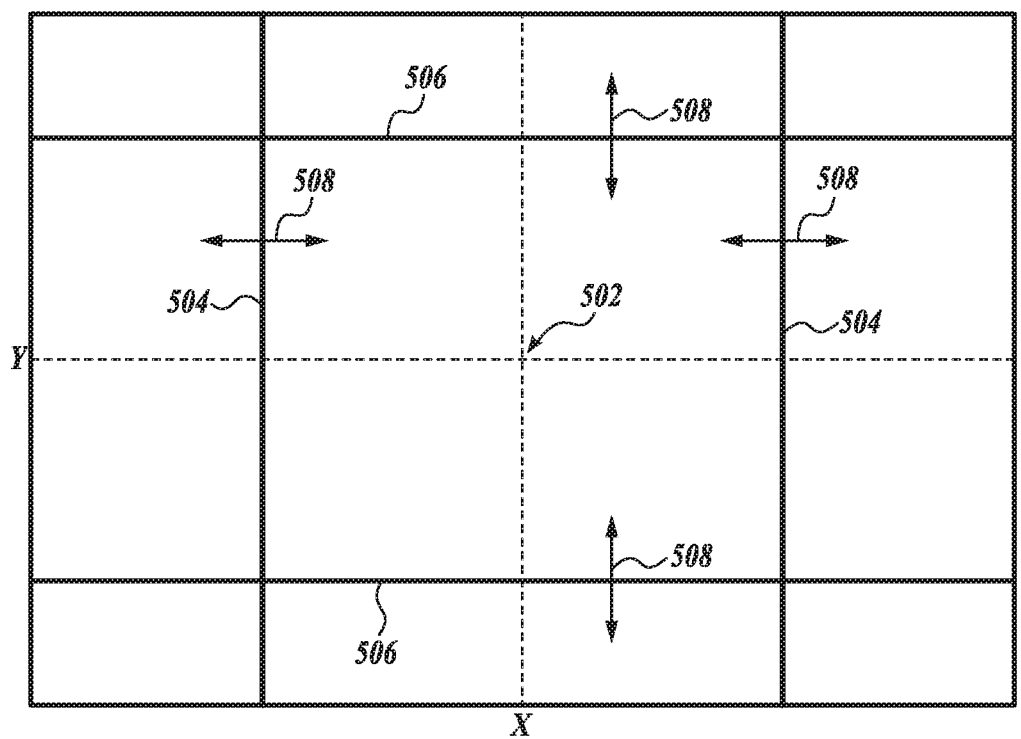
FIG. 5 is an alignment image displayed by a dynamic fixation target based on a position of an eye relative to an eyepiece lens assembly, in accordance with an embodiment of the disclosure.

FIG. 5 is an alignment image displayed by a dynamic fixation target based on a position of an eye relative to an eyepiece lens assembly, in accordance with an embodiment of the disclosure. The image includes crosshairs 502 (shown as dashed lines) disposed at a center of the alignment image, solid lines 504 and 506 defining a square about the crosshairs 502, and arrows 508 adjacent to the solid lines 504 and 506. In an embodiment, positions of the solid lines 504 and 506 are based upon a position of a user's eye relative to an eyepiece lens assembly of a retinal imaging system. In this regard, a position of a set of the solid lines 504 and 506 may be based on a position of the eye with respect to one or more coordinates. For example, a position of the vertical solid lines 504 may be based upon a position of the eye relative to the eyepiece lens assembly along an X axis, whereas a position of the horizontal solid lines 506 may be based upon a position of the eye relative to the eyepiece lens assembly along a Y axis. In an embodiment, the horizontal solid lines 506 and vertical solid lines 504 have different colors.

Such an alignment image presenting indications of lateral misalignment is suitable for use with retinal imaging systems in which a displacement of the user's eye relative to the eyepiece lens assembly is fixed. In an embodiment, the alignment image includes lines converging on the crosshairs (not shown, see FIG. 6) providing an indication of alignment of the eye fore/aft with respect to the eyepiece lens assembly.

In an embodiment, a position of the crosshairs 502 is based upon an ideal alignment of an eye relative to an eyepiece lens assembly. In an embodiment, the arrows 508 indicate one or more directions and/or distances along which a user's eye should travel to bring the eye within a threshold misalignment, such as to bring the eye within an eyebox of the retinal imaging system. As alignment is gradually achieved the horizontal lines 506 and vertical lines 504 converge towards the center of crosshairs 502 providing an indication of alignment.

Figure 6:
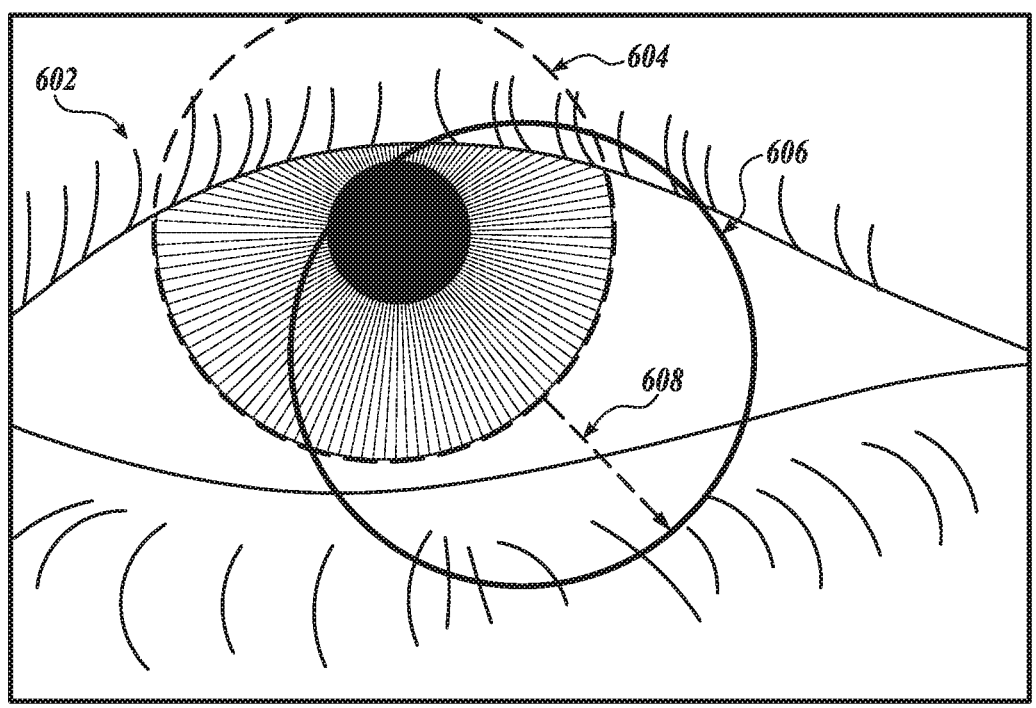
FIG. 6 is an alignment image displayed by a dynamic fixation target based on a position of an eye relative to an eyepiece lens assembly, in accordance with an embodiment of the disclosure.

FIG. 6 is an alignment image displayed by a dynamic fixation target based on a position of an eye relative to an eyepiece lens assembly, in accordance with an embodiment of the disclosure. As shown, FIG. 6 includes representation, such as a picture, of a user's eye 602 including a dashed line 604 about an iris of the eye 602 and a circle 606 shown disposed away from a center of the representation of the user's eye 602. In an embodiment, the circle 606 is representative of a position of the eye 602 within an eyebox of a retinal imaging system. The image is shown to further include an arrow 608 between an edge of the dashed lines 604 and an edge of the circle 606. As the user's eye 602 travels in the direction of the arrow 608, the eye 602 travels to within the eyebox of the retinal imaging system. In this regard, the arrow 608 indicates a lateral direction along which the user's eye 602 should travel to achieve alignment of the eye 602 once within the eyebox, such as within the threshold misalignment, when the eye 602 is suitably positioned for retinal imaging by a retinal imaging system.

In an embodiment, a color of the circle 606 indicates a fore/aft misalignment of the eye 602 with respect to the eyepiece lens assembly. In an embodiment, the color of the circle 606 changes as a degree of fore/aft misalignment of the eye 602 changes. In this regard, the alignment image comprises a representation of one or more of a lateral position of the eye 602 relative to the eyepiece lens assembly and an eye relief position of the eye relative to the eyepiece lens assembly. Likewise, in an embodiment, the representation of the eye relief position relative to the eyepiece lens assembly is represented by one or more colors displayed in the image. In this regard, the color of the circle 606 indicates an extent to which the user's eye 602 should travel back or forth to achieve alignment with the eyepiece lens assembly.

Figure 12:
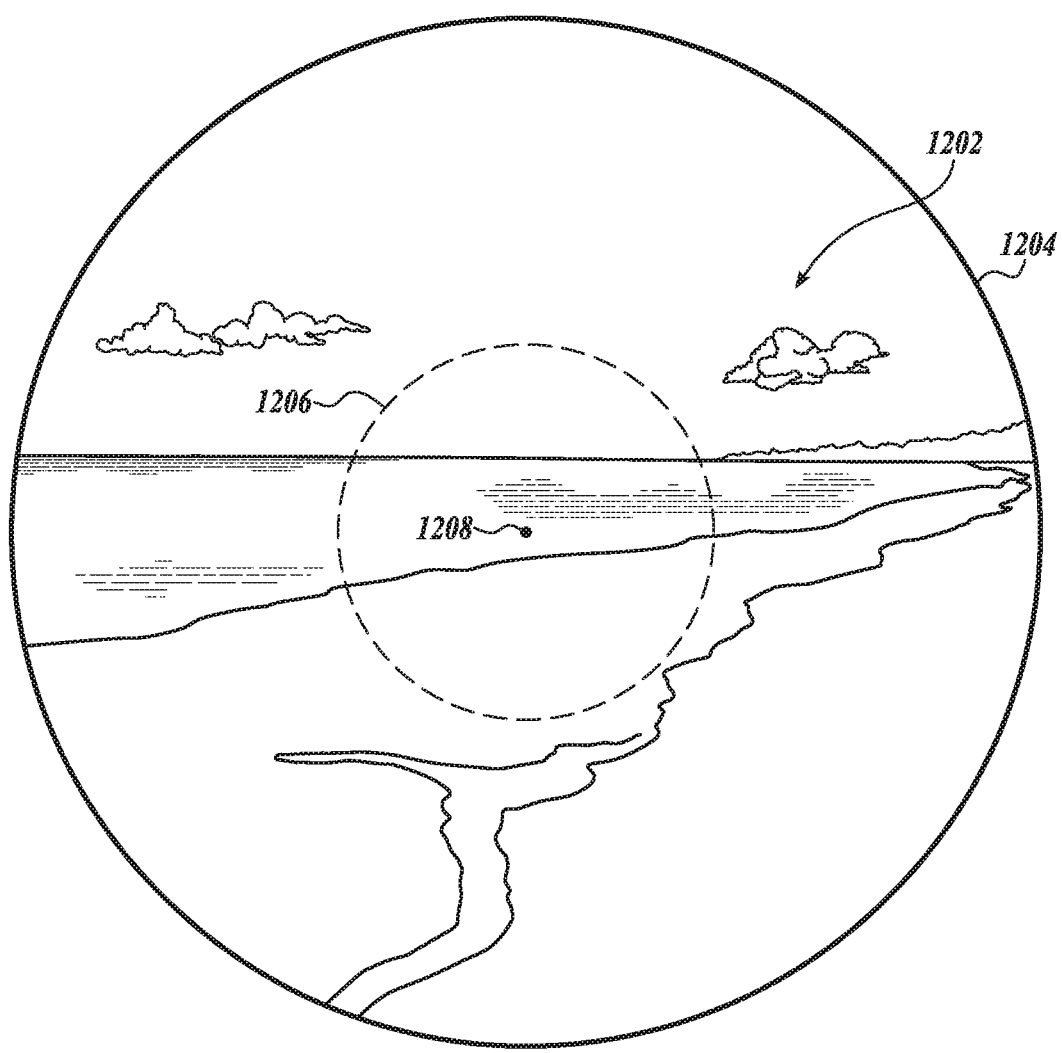
FIG. 12 is an alignment image displayed by a dynamic fixation target based on a position of an eye relative to an eyepiece lens assembly, in accordance with an embodiment of the disclosure.

FIG. 12 is an alignment image displayed by a dynamic fixation target based on a position of an eye relative to an eyepiece lens assembly, in accordance with an embodiment of the disclosure. As shown, FIG. 12 includes an alignment image, here a scene 1202 of a beach, encircled by a solid line 1204. In an embodiment, the alignment image is slowly magnified with a position of the user's eye relative to the eyepiece lens assembly controlling an orientation and/or magnification of the image. In that regard, a position of the user's eye controls what portion of the alignment image is disposed in a center of the circle. When a user's eye is laterally aligned with the eyepiece lens assembly, a central portion 1206 of the alignment image is disposed in the center 1208 of the circle 1204. Likewise, in an embodiment, a degree of magnification of the alignment image is controlled by alignment of the user's eye fore/aft with respect to the eyepiece lens assembly.

As above, in an embodiment, the displays of the retinal imaging systems described herein are configured to generate alignment images displaying, for example, games to a user presenting strategic goals to aid in aligning users' eyes with the retinal imaging systems. In that regard, attention is directed in particular to FIGS. 7-10.

Figure 7:
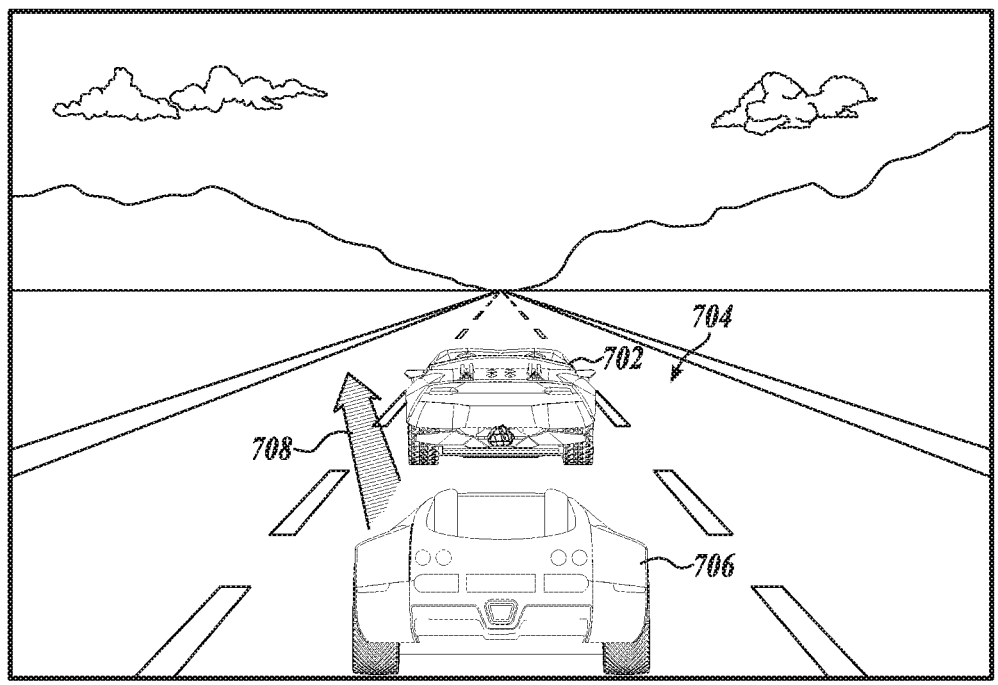
FIG. 7 is an alignment image displayed by a dynamic fixation target based on a position of an eye relative to an eyepiece lens assembly, in accordance with an embodiment of the disclosure.

FIG. 7 is an alignment image displayed by a dynamic fixation target based on a position of an eye relative to an eyepiece lens assembly, in accordance with an embodiment of the disclosure. The alignment image of FIG. 7 is shown to include a first car 702 travelling on a road 704, a second car 706 behind the first car 702, and an arrow 704 indicating a direction along which the second car 706 should travel. In an embodiment, a position of the second car 706 is based upon a position of the user's eye relative to an eyepiece lens assembly of a retinal imaging system of the present disclosure. If the user's eye is misaligned with respect to the eyepiece lens assembly of the retinal imaging system, the display may, in an embodiment, generate and display an alignment image showing an obstacle, here the first car 702, for the second car 706 to avoid as it travels down the road 704, such as by moving to the left and forward as suggested by the arrow 708. Accordingly, when a user moves their eye laterally and/or fore/aft, the display correspondingly generates an image in which an object, here the second car 706 moves, laterally and/or fore/aft as prompted by the alignment image to avoid the object, here the first car 702. In this regard, strategic goals presented by the display to the user are used to achieve alignment of the user's eye with respect to the eyepiece lens assembly of the retinal imaging system.

Figure 8:
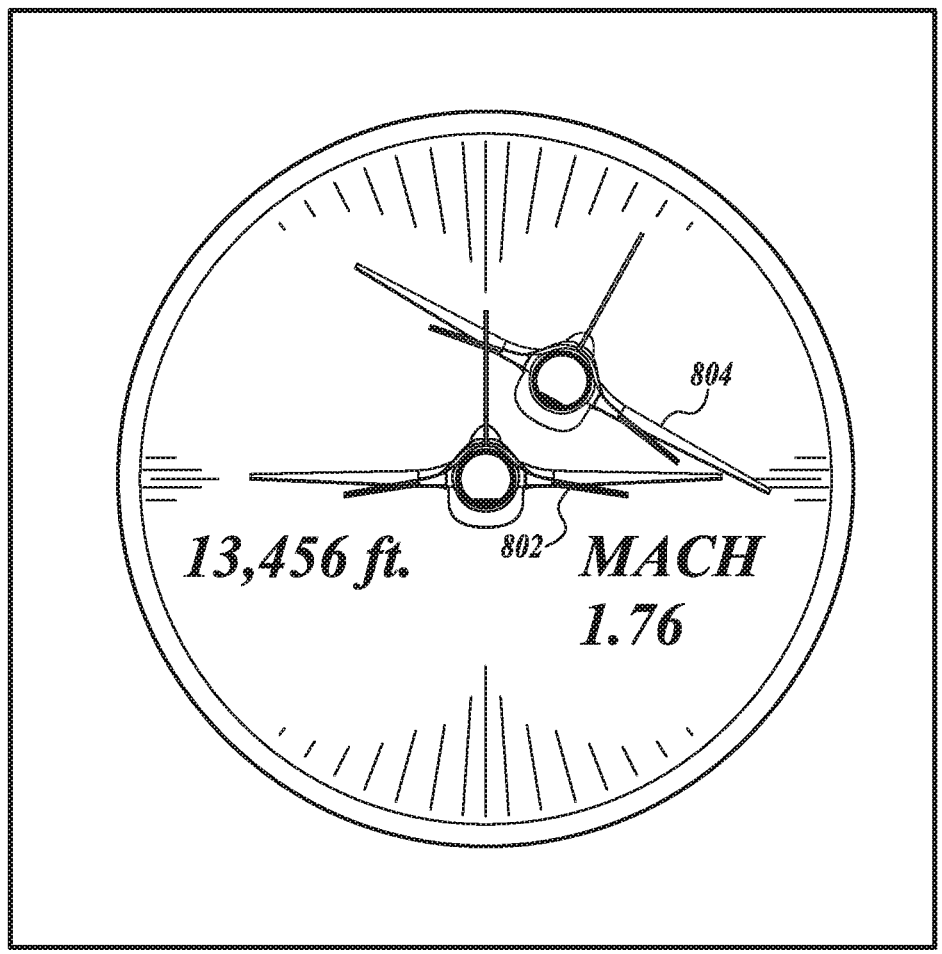
FIG. 8 is an alignment image displayed by a dynamic fixation target based on a position of an eye relative to an eyepiece lens assembly, in accordance with an embodiment of the disclosure.

FIG. 8 is an alignment image displayed by a dynamic fixation target based on a position of an eye relative to an eyepiece lens assembly, in accordance with an embodiment of the disclosure. The illustrated alignment image includes a rear view of a first plane 802 and a rear view of a second plane 804 shown disposed above and to the right of the first plane 802. In this regard, in an embodiment, the representation of the position of the eye relative to the eyepiece lens assembly and the representation of the aligned eye position do not completely overlap when there is any misalignment between the eye and the eyepiece lens assembly.

In an embodiment, a position of the second plane 804 is based on a position of a user's eye relative to an eyepiece lens assembly. In an embodiment, a position of the first plane 802 is based on a position of a user's eye aligned with respect to an eyepiece lens assembly of the retinal imaging system. As shown, the second plane 804 is above and to the right of the first plane 802. As user's eye moves closer to alignment, such as, in the illustrated embodiment, by moving the eye down and to the left, the display adjusts to generate additional alignment images in which the second plane 804 is shown to move closer to overlapping with the first plane 802. In this regard, the display is configured to generate images presenting strategic goals encouraging alignment of the user's eye with respect to an eyepiece lens assembly of the retinal imaging system.

Figure 9:
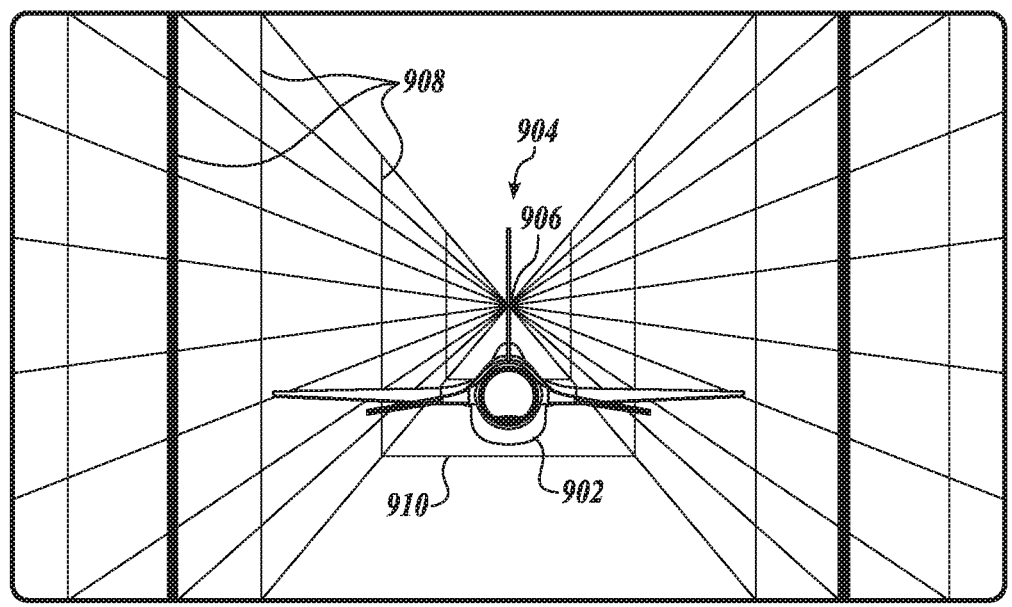
FIG. 9 is an alignment image displayed by a dynamic fixation target based on a position of an eye relative to an eyepiece lens assembly, in accordance with an embodiment of the disclosure.

FIG. 9 is an alignment image displayed by a dynamic fixation target based on a position of an eye relative to an eyepiece lens assembly, in accordance with an embodiment of the disclosure. FIG. 9 includes an illustration of a spaceship 902 travelling down a corridor 904. In an embodiment, a position of the spaceship 902 in the alignment image is based on a position of a user's eye relative to an eyepiece lens assembly of a retinal imaging system. As a user's moves the eye relative to the eyepiece lens assembly, the display adjusts the alignment image generated to move the spaceship 902 within and down the corridor 904. In an embodiment, as alignment of the eye with respect to the eyepiece lens assembly is achieved the display generates an alignment image of the spaceship 902 moving down the center 906 of the narrowing corridor 904. In this regard, the display generates one or more alignment images presenting strategic goals to the user to move an eye laterally and back/forth relative to the eyepiece lens assembly to achieve alignment. While a spaceship 902 is shown, it will be understood that other representations, such as crosshairs, may be used to indicate lateral alignment of the eye relative to the eyepiece lens assembly.

As shown, the alignment image including the corridor 904 includes horizontal lines 910 and vertical lines 908. In an embodiment, a position of the user's eye relative to the eyepiece lens assembly controls which such horizontal lines 910 and vertical lines 908 change color, are darkened, lightened, or otherwise changed with respect to other horizontal lines 910 and vertical lines 908. In this regard, the alignment image provides an indication of fore/aft alignment of the user's eye with respect to the eyepiece lens assembly.

Figure 10:
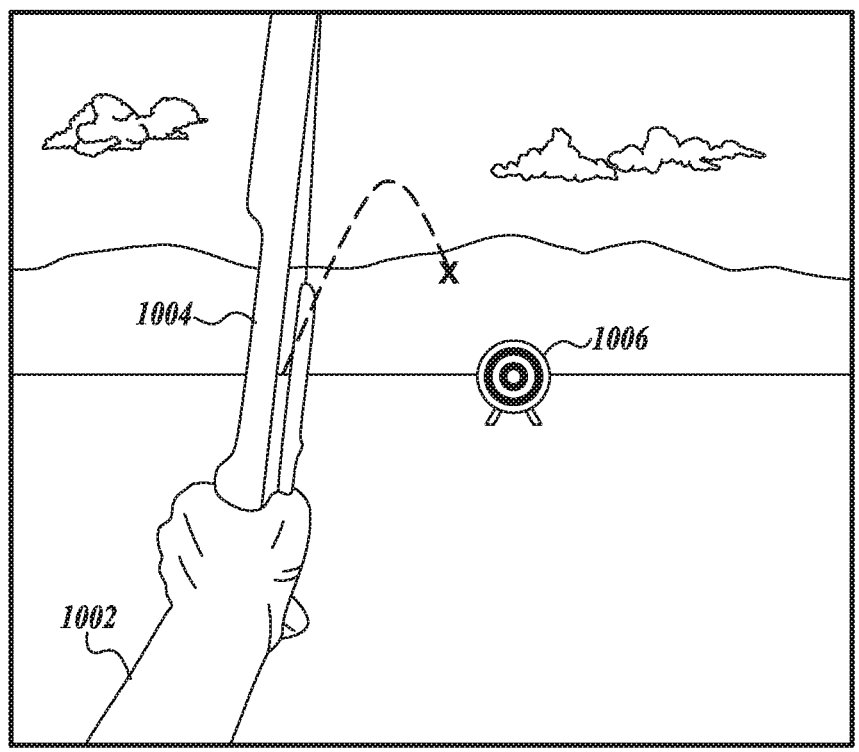
FIG. 10 is an alignment image displayed by a dynamic fixation target based on a position of an eye relative to an eyepiece lens assembly, in accordance with an embodiment of the disclosure.

FIG. 10 is an alignment image displayed by a dynamic fixation target based on a position of an eye relative to an eyepiece lens assembly, in accordance with an embodiment of the disclosure. The alignment image of FIG. 10 includes an illustration of an archer 1002 aiming a bow and arrow 1004, a target 1006, and an X indicating a trajectory of the arrow 1004. In an embodiment, the X is based upon a position of a user's eye relative to an eyepiece lens assembly. In an embodiment, the target 1006 is based on a position of a user's eye that is aligned with respect to the eyepiece lens assembly. As a user moves their eye, the display adjusts the alignment image to correspondingly move the X, such as towards or onto the target 1006, as the user's eye moves toward or within an eyebox of the retinal imaging system. In this regard, the display is configured to generate alignment images indicating one or more directions along which the user should move their eye to achieve alignment with the eyepiece lens assembly.

Figure 11A:
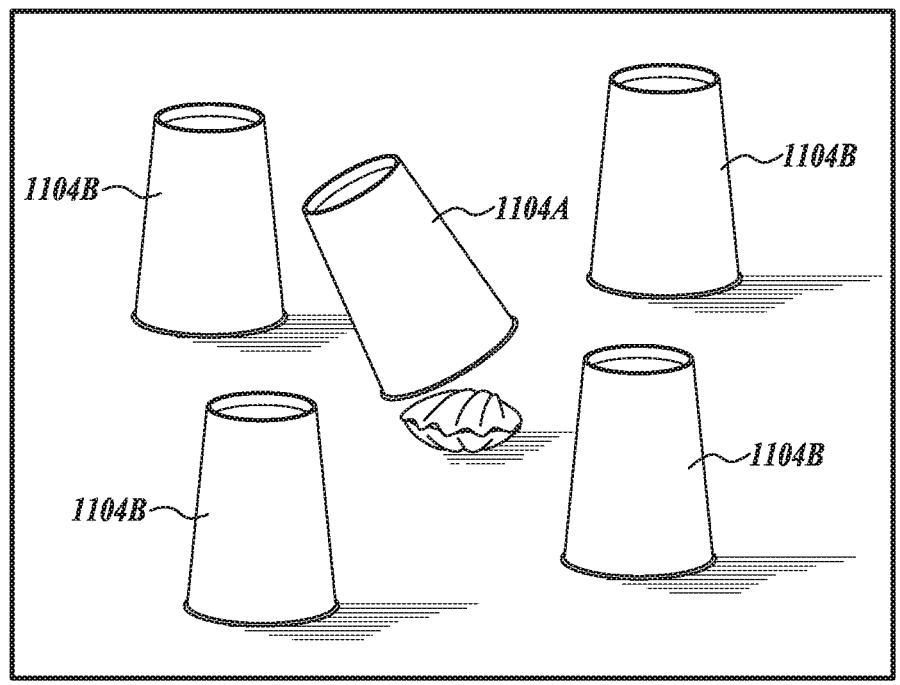
FIGS. 11A and 11B are pupil dilation images displayed by a dynamic fixation target, in accordance with an embodiment of the disclosure.
Figure 11B:
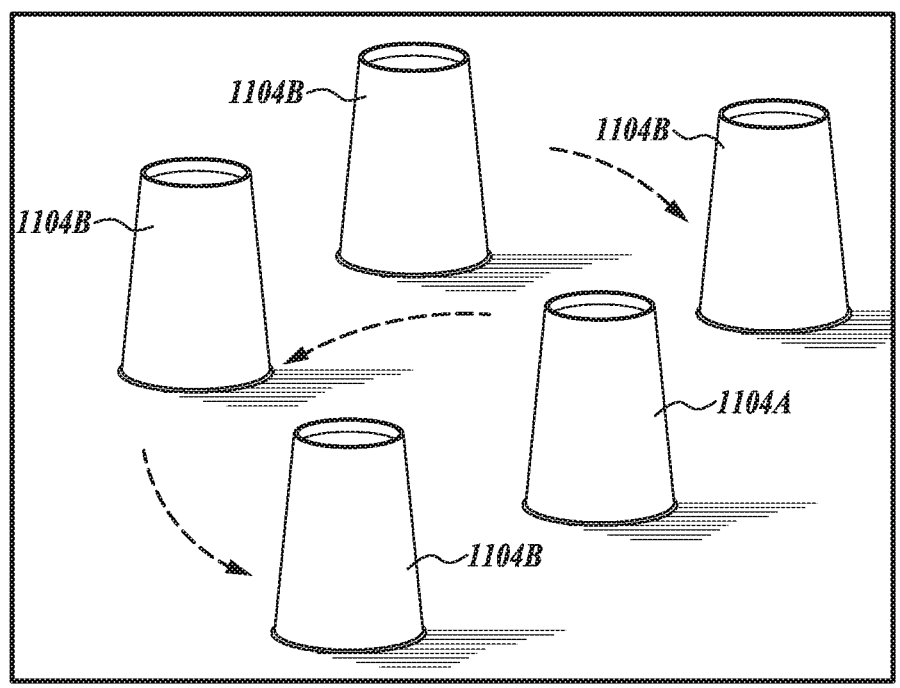

As above, retinal image quality may be affected by pupil dilation. In an embodiment, a controller of a retinal imaging system described herein operates a display, such as display 225, to output an image configured to widen the pupil of an eye. In general, a pupil of an eye will widen when a user views, for example, a challenging puzzle or a problem, suitable, for example, for retinal imaging. In that regard, attention is directed to FIGS. 11A and 11B, showing pupil dilation images displayed by a dynamic fixation target, in accordance with an embodiment of the disclosure. As shown in FIG. 11A, a shell 1102 is placed underneath one cup 1104A of a number of cups 1104A and 1104B. In FIG. 11B, the cups 1104A and 1104B are shown moving. In this regard, a user is encouraged to follow the cup 1104A under which the shell 1102 is disposed, presenting a puzzle for the user to solve, thus generally widening a pupil of a user's eye.

While a cup game is illustrated, it will be understood that other games, puzzles, and problems may be used. In this regard, the pupil dilation image may present an arithmetic problem, a logic puzzle, and the like suitable to widen a pupil of a user's eye for retinal imaging.

Likewise, a pupil of an eye will generally widen when a user views a startling or evocative image. In that regard, in an embodiment, the controller of a retinal imaging system described herein, such as controller 215 of retinal imaging system 200, operates a display, such as display 225, to output a pupil dilation image meant to evoke an emotional response in a user, such as an animal in a threatening position.

Such pupil dilation images suitable for pupil dilation may be used in conjunction with other images, such as alignment images, described herein to align a user's eye relative to an eyepiece lens assembly. In that regard, images generated by the displays of the retinal imaging systems are suitable achieve pupil dilation, aligned eye position, and eye gaze vector suitable for retinal imaging.

In an embodiment, the display is configured to generate a pupil dilation image configured to widen a pupil of a user's eye after the user's eye is aligned with an eyepiece lens assembly of the retinal imaging system. In an embodiment, the display is configured to generate the pupil dilation image interspersed with alignment images configured to encourage alignment of the user's eye with the eyepiece lens assembly.

In another aspect, the present disclosure provides a method of obtaining a retinal image of an eye. In an embodiment, the method comprises acquiring a first image of the eye; analyzing the first image to determine whether any misalignment between the eye and an eyepiece lens assembly of a retinal imaging system is greater than a threshold misalignment; in response to determining whether any misalignment is greater than the threshold misalignment, adjusting a dynamic fixation target of the retinal imaging system based on a position of the eye relative to the eyepiece lens assembly; and acquiring the retinal image of the eye while the eye is positioned within the threshold misalignment. In an embodiment, the methods are suitable to be performed on or with the retinal imaging systems of the present disclosure. As described further herein, in an embodiment, the threshold misalignment is based upon an eyebox of a retinal imaging system.

In an embodiment, adjusting the dynamic fixation target is as described further herein with respect to the retinal imaging systems of the present disclosure and, in particular, with respect to the alignment and pupil dilation images of FIGS. 3-10, 11A, 11B, and 12 of the present disclosure.

In an embodiment, the method of the present disclosure further includes displaying, with the dynamic fixation target, a pupil dilation image configured to dilate a pupil of the eye. In an embodiment, the pupil dilation image includes a representation of a problem to be solved by a user.

In some embodiment, the order in which some or all of the steps are described in each process should not be deemed limiting. Rather, one of ordinary skill in the art having the benefit of the present disclosure will understand that some of the steps may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described.

Accordingly, in an aspect, the present disclosure provides non-transitory, machine-readable storage medium having instructions stored thereon, which when executed by a processing system, cause the processing system to perform operations comprising the methods of the present disclosure. In an embodiment, the non-transitory, machine-readable storage media of the present disclosure are suitable for use with the retinal imaging systems described herein, such as with retinal imaging system 200, to achieve or encourage alignment of a user's eye with the retinal imaging system suitable for retinal imaging. In an embodiment, the non-transitory, machine-readable storage medium has instructions stored thereon, which when executed by a processing system, cause the processing system to perform operations comprising acquiring a first image of an eye; analyzing the first image to determine whether any misalignment between the eye and an eyepiece lens assembly of a retinal imaging system is greater than a threshold misalignment; in response to determining whether any misalignment is greater than the threshold misalignment, adjusting a dynamic fixation target of the retinal imaging system based on a position of the eye relative to the eyepiece lens assembly; and acquiring the retinal image of the eye while the eye is positioned within the threshold misalignment.

In an embodiment, adjusting the dynamic fixation target includes displaying an alignment image with the dynamic fixation target based upon a position of the eye relative to the eyepiece lens assembly. In an embodiment, adjusting the dynamic fixation target includes moving an element of the alignment image based upon a position of the eye relative to the eyepiece lens assembly. In an embodiment, the alignment image includes a representation of the position of the eye relative to the eyepiece lens assembly and a representation of an aligned eye position that is under the threshold misalignment. In an embodiment, the alignment image includes a representation of the threshold misalignment.

In an embodiment, the non-transitory, machine-readable storage medium has instructions stored thereon, which when executed by a processing system, cause the processing system to perform operations comprising displaying, with the dynamic fixation target, a pupil dilation image configured to dilate a pupil of the eye. In an embodiment, the pupil dilation image includes a representation of a problem to be solved by a user.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.). Additionally, the processes may be embodied within hardware, such as an application specific integrated circuit ("ASIC") or otherwise.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A retinal imaging system, comprising:
    an eyepiece lens assembly;
    an image sensor adapted to acquire a retinal image of an eye through the eyepiece lens assembly;
    a dynamic fixation target optically coupled to the eyepiece lens assembly such that the dynamic fixation target is viewable through the eyepiece lens assembly by the eye; and
    a controller communicatively coupled to the image sensor and the dynamic fixation target, the controller including logic that, when executed by the controller, causes the retinal imaging system to perform operations including:
        acquiring a first image of the eye;
        analyzing the first image to determine whether any misalignment between the eye and the eyepiece lens assembly is greater than a threshold misalignment;
        in response to determining whether any misalignment is greater than the threshold misalignment, adjusting the dynamic fixation target based on a position of the eye relative to the eyepiece lens assembly; and
        acquiring the retinal image of the eye while the eye is positioned within the threshold misalignment.

2. The retinal imaging system of claim 1, wherein adjusting the dynamic fixation target includes displaying an alignment image with the dynamic fixation target based upon a position of the eye relative to the eyepiece lens assembly.

3. The retinal imaging system of claim 2, wherein adjusting the dynamic fixation target includes moving an element of the alignment image based upon the position of the eye relative to the eyepiece lens assembly.

4. The retinal imaging system of claim 2, wherein the alignment image includes a representation of the position of the eye relative to the eyepiece lens assembly and a representation of an aligned eye position that is under the threshold misalignment.

5. The retinal imaging system of claim 4, wherein the representation of the position of the eye relative to the eyepiece lens assembly and the representation of the aligned eye position do not completely overlap when there is any misalignment between the eye and the eyepiece lens assembly.

6. The retinal imaging system of claim 4, the alignment image includes a representation of a direction in which to move the eye to achieve alignment of the eye with the eyepiece lens assembly.

7. The retinal imaging system of claim 2, wherein the alignment image includes a representation of the threshold misalignment.

8. The retinal imaging system of claim 7, wherein adjusting the alignment image includes changing a size of the representation of the threshold misalignment changes based on an alignment between the eye and the eyepiece lens assembly.

9. The retinal imaging system of claim 2, wherein the alignment image comprises a representation of one or more of a lateral position of the eye relative to the eyepiece lens assembly and an eye relief position of the eye relative to the eyepiece lens assembly.

10. The retinal imaging system of claim 9, wherein the representation of the eye relief position relative to the eyepiece lens assembly is represented by one or more colors displayed in the image.

11. The retinal imaging system of claim 1, wherein adjusting the dynamic fixation target based on the position of the eye relative to the eyepiece lens assembly presents strategic goals for a user to achieve alignment of the eye position relative to the eyepiece lens assembly.

12. The retinal imaging system of claim 1, wherein the controller further includes logic that, when executed by the controller, causes the retinal imaging system to perform operations including:
    displaying, with the dynamic fixation target, a pupil dilation image configured to dilate a pupil of the eye.

13. The retinal imaging system of claim 12, wherein the pupil dilation image includes a representation of a problem to be solved by a user.

14. The retinal imaging system of claim 1, wherein the threshold misalignment is based on an eyebox of the retinal imaging system.

15. A non-transitory, machine-readable storage medium having instructions stored thereon, which when executed by a processing system, cause the processing system to perform operations comprising:
    acquiring a first image of an eye;
    analyzing the first image to determine whether any misalignment between the eye and an eyepiece lens assembly of a retinal imaging system is greater than a threshold misalignment;
    in response to determining whether any misalignment is greater than the threshold misalignment, adjusting a dynamic fixation target of the retinal imaging system based on a position of the eye relative to the eyepiece lens assembly;
    displaying the dynamic fixation target to the eye; and
    acquiring a retinal image of the eye while the eye is positioned within the threshold misalignment.

16. The non-transitory, machine-readable storage medium of claim 15, wherein adjusting the dynamic fixation target includes displaying an alignment image with the dynamic fixation target based upon the position of the eye relative to the eyepiece lens assembly.

17. The non-transitory, machine-readable storage medium of claim 16, wherein adjusting the dynamic fixation target includes moving an element of the alignment image based upon the position of the eye relative to the eyepiece lens assembly.

18. The non-transitory, machine-readable storage medium of claim 16, wherein the alignment image includes a representation of the position of the eye relative to the eyepiece lens assembly and a representation of an aligned eye position that is under the threshold misalignment.

19. The non-transitory, machine-readable storage medium of claim 16, wherein the image includes a representation of the threshold misalignment.

20. A method of obtaining a retinal image of an eye, the method comprising:
- acquiring a first image of the eye;
- analyzing the first image to determine whether any misalignment between the eye and an eyepiece lens assembly of a retinal imaging system is greater than a threshold misalignment;
- in response to determining whether any misalignment is greater than the threshold misalignment, adjusting a dynamic fixation target of the retinal imaging system based on a position of the eye relative to the eyepiece lens assembly;
- displaying the dynamic fixation target to the eye; and
- acquiring the retinal image of the eye while the eye is positioned within the threshold misalignment.

* * * * *